(12) United States Patent
Olson

(10) Patent No.: US 9,901,303 B2
(45) Date of Patent: Feb. 27, 2018

(54) SYSTEM AND METHOD FOR REGISTRATION OF MULTIPLE NAVIGATION SYSTEMS TO A COMMON COORDINATE FRAME

(75) Inventor: Eric S. Olson, Maplewood, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 291 days.

(21) Appl. No.: 13/087,203

(22) Filed: Apr. 14, 2011

(65) Prior Publication Data
US 2012/0265054 A1    Oct. 18, 2012

(51) Int. Cl.
*A61B 5/00*    (2006.01)
*A61B 5/06*    (2006.01)
(Continued)

(52) U.S. Cl.
CPC ............ *A61B 5/6852* (2013.01); *A61B 5/062* (2013.01); *A61B 5/063* (2013.01); *A61B 34/20* (2016.02);
(Continued)

(58) Field of Classification Search
CPC ....... A61B 5/6852; A61B 90/39; A61B 34/20; A61B 5/063; A61B 5/062;
(Continued)

(56) References Cited

U.S. PATENT DOCUMENTS

| 5,297,549 A | 3/1994 | Beatty et al. |
|---|---|---|
| 5,391,199 A | 2/1995 | Ben-Haim |

(Continued)

FOREIGN PATENT DOCUMENTS

| CN | 101782358 | 7/2010 |
|---|---|---|
| CN | 103298516 | 9/2013 |

(Continued)

OTHER PUBLICATIONS

International Search Report and Written Opinion issued in PCT/US12/22678, dated May 30, 2012.
(Continued)

*Primary Examiner* — Amanda Lauritzen
*Assistant Examiner* — Lisa Kinnard
(74) *Attorney, Agent, or Firm* — Wiley Rein LLP

(57) ABSTRACT

A method of registering two or more localization systems utilizing unique coordinate frames A and B to a common coordinate frames includes measuring position information for one or more reference locations r in each coordinate frame (e.g., $A_r$ and $B_r$). For each reference location, a fiducial grouping is created from the respective position measurements (e.g., ($A_r$, $B_r$)). The fiducial groupings are used to generate a mapping function $f$ that transforms position measurements expressed relative to the second coordinate frame B to the first coordinate frame A. The mapping function $f$ is defined such that a distance between $f(B_r)$ and $A_r$ is about zero for each reference location r. Each localization system may also measure position information for a respective fixed reference localization element. Divergence between these fixed reference localization elements in the common coordinate system may be used to monitor, signal, and correct for anomalies such as dislodgement and drift.

20 Claims, 3 Drawing Sheets

(51) Int. Cl.
 A61B 90/00 (2016.01)
 A61B 34/20 (2016.01)
(52) U.S. Cl.
 CPC ...... *A61B 90/39* (2016.02); *A61B 2034/2051* (2016.02); *A61B 2034/2053* (2016.02); *A61B 2090/0818* (2016.02); *A61B 2090/3995* (2016.02)
(58) Field of Classification Search
 CPC .... A61B 2034/2051; A61B 2090/3995; A61B 2090/0818; A61B 2034/2053
 USPC ........................................................ 600/424
 See application file for complete search history.

(56) References Cited

U.S. PATENT DOCUMENTS

| | | | |
|---|---|---|---|
| 5,443,489 A | 8/1995 | Ben-Haim | |
| 5,480,422 A | 1/1996 | Ben-Haim | |
| 5,546,951 A | 8/1996 | Ben-Haim | |
| 5,568,809 A | 10/1996 | Ben-Haim | |
| 5,662,108 A | 9/1997 | Budd et al. | |
| 5,694,945 A | 12/1997 | Ben-Haim | |
| 5,697,337 A | 12/1997 | Wittkampf | |
| 5,697,377 A | 12/1997 | Wittkampf | |
| 5,718,241 A | 2/1998 | Ben-Haim et al. | |
| 5,738,096 A | 4/1998 | Ben-Haim | |
| 5,840,025 A | 11/1998 | Ben-Haim | |
| 5,944,022 A | 8/1999 | Nardella et al. | |
| 5,954,665 A | 9/1999 | Ben-Haim | |
| 5,983,126 A | 11/1999 | Wittkampf | |
| 6,016,439 A | 1/2000 | Acker | |
| 6,063,022 A | 5/2000 | Ben-Haim | |
| 6,066,094 A | 5/2000 | Ben-Haim | |
| 6,226,542 B1 | 5/2001 | Reisfeld | |
| 6,233,476 B1 | 5/2001 | Strommer | |
| 6,288,785 B1 | 9/2001 | Frantz | |
| 6,301,496 B1 | 10/2001 | Reisfeld | |
| 6,640,119 B1 | 10/2003 | Budd et al. | |
| 6,728,562 B1 | 4/2004 | Budd et al. | |
| 6,939,309 B1 | 9/2005 | Beatty et al. | |
| 6,947,785 B1 | 9/2005 | Beatty et al. | |
| 6,978,168 B2 | 12/2005 | Beatty et al. | |
| 6,990,370 B1 | 1/2006 | Beatty et al. | |
| 7,072,707 B2 | 7/2006 | Galloway | |
| 7,088,099 B2 | 8/2006 | Doddrell | |
| 7,187,810 B2 | 3/2007 | Clune et al. | |
| 7,197,354 B2 | 3/2007 | Sobe | |
| 7,263,397 B2 | 8/2007 | Hauck | |
| 7,379,769 B2 | 5/2008 | Piron | |
| 7,386,339 B2 | 6/2008 | Strommer | |
| 7,536,218 B2 | 5/2009 | Govari | |
| 7,583,275 B2* | 9/2009 | Neumann et al. ............ 345/633 |
| 7,672,504 B2* | 3/2010 | Childers ................ G01B 11/24 348/211.11 |
| 7,747,305 B2 | 6/2010 | Dean | |
| 8,111,058 B2 | 2/2012 | King et al. | |
| 8,326,419 B2 | 12/2012 | Rosenberg et al. | |
| 8,473,216 B2* | 6/2013 | Sun ........................ C12Q 1/686 702/19 |
| 8,569,706 B2 | 10/2013 | Thiruvenkadam et al. | |
| 9,271,664 B2 | 3/2016 | Wedan et al. | |
| 2003/0093004 A1 | 5/2003 | Sosa et al. | |
| 2004/0097806 A1 | 5/2004 | Hunter et al. | |
| 2004/0254437 A1 | 12/2004 | Hauck et al. | |
| 2005/0057246 A1 | 3/2005 | Orozco et al. | |
| 2005/0137478 A1 | 6/2005 | Younge et al. | |
| 2005/0222554 A1 | 10/2005 | Wallace et al. | |
| 2005/0288577 A1 | 12/2005 | Weese | |
| 2006/0084867 A1 | 4/2006 | Tremblay et al. | |
| 2006/0095022 A1 | 5/2006 | Moll et al. | |
| 2006/0100610 A1 | 5/2006 | Wallace et al. | |
| 2007/0016007 A1* | 1/2007 | Govari et al. ................ 600/424 |
| 2007/0055331 A1 | 3/2007 | Merfeld | |
| 2007/0060833 A1 | 3/2007 | Hauck | |
| 2007/0110665 A1* | 5/2007 | Bolan ................ A61K 49/0002 424/1.11 |
| 2007/0181139 A1 | 8/2007 | Hauck | |
| 2008/0161681 A1 | 7/2008 | Hauck | |
| 2008/0221425 A1* | 9/2008 | Olson .................... A61B 90/36 600/407 |
| 2008/0221643 A1 | 9/2008 | Olson | |
| 2009/0028416 A1* | 1/2009 | Floeder .............. G01N 21/8851 382/141 |
| 2009/0067755 A1 | 3/2009 | Khamene et al. | |
| 2009/0161827 A1* | 6/2009 | Gertner et al. ................. 378/65 |
| 2009/0198126 A1 | 8/2009 | Klingenbeck-Regn | |
| 2010/0079158 A1 | 4/2010 | Bar-Tal et al. | |
| 2010/0149183 A1 | 6/2010 | Loewke et al. | |
| 2010/0152571 A1 | 6/2010 | Hartmann et al. | |
| 2010/0268059 A1 | 10/2010 | Ryu et al. | |
| 2010/0298826 A1 | 11/2010 | Leo et al. | |
| 2011/0062344 A1 | 3/2011 | Kornblau et al. | |
| 2011/0158488 A1 | 6/2011 | Cohen | |
| 2011/0160569 A1 | 6/2011 | Cohen | |
| 2011/0160593 A1* | 6/2011 | Deno ........................ A61B 5/06 600/463 |
| 2011/0166407 A1* | 7/2011 | Sumanaweera ...... A61B 5/0422 600/1 |
| 2011/0172927 A1 | 7/2011 | Sahasrabudhe | |
| 2011/0267340 A1 | 11/2011 | Kraus et al. | |
| 2012/0172702 A1 | 7/2012 | Koyrakh | |
| 2012/0172724 A1* | 7/2012 | Hill .......................... A61B 8/12 600/443 |
| 2012/0265054 A1 | 10/2012 | Olson | |

FOREIGN PATENT DOCUMENTS

| | | |
|---|---|---|
| EP | 1743575 | 1/2007 |
| EP | 2168478 | 3/2010 |
| JP | 2006072933 | 3/2006 |
| JP | 2007-21218 | 2/2007 |
| JP | 2010-520780 | 6/2010 |
| WO | 1994/004938 | 3/1994 |
| WO | 1995/005768 | 2/1996 |
| WO | 1998/040026 | 9/1998 |
| WO | 2001/006917 | 2/2001 |
| WO | WO 2008083111 A1 * | 7/2008 ............... A61B 5/06 |
| WO | 2008/112039 | 9/2008 |
| WO | 2008/112420 | 9/2008 |

OTHER PUBLICATIONS

Schaefer & Warren, Mean Value Coordinates for Closed Triangular Meshes, ACM Transactions on Graphics, 24(3):561-66 (Jul. 2005).
U.S. Appl. No. 11/715,919, filed Mar. 9, 2007, Olson et al.
Wiley, D. F., Evolutionary Morphing, Proceedings of IEEE Visualization, 2005, pp. 431-438.
Jain, A. K., et al., FTRAC—A robust fluoroscope tracking fiducial, Medical Physics, Oct. 2005, pp. 3185-3198, vol. 32, No. 10.
Chui, H., et al., A New Algorithm for Non-Rigid Point Matching, Proceeding, IEEE Conference on Computer Vision and Pattern, 2000, pp. 44-51, vol. 2.
Ju, T., et al., Mean Value Coordinates for Closed Triangular Meshes, ACM Transactions on Graphics, 24(3): 561-66 (Jul. 2005).
Orr, M. J. L., Introduction to Radial Basis Function Networks, 1996, pp. 1-67.
Ebeling, H., et al., ASMOOTH: A simple and efficient algorithm for adaptive kernel smoothing of two-dimensional imaging data, Mon. Not. R. Astron. Soc. 2006, pp. 65-73, vol. 368.
International Search Report and Written Opinion issued in PCT/US08/54969, dated Aug. 15, 2008.
Bookstein, F. L., Principal Warps: Thin-Plate Splines and the Decomposition of Deformations, IEEE Transactions on Pattern Analysis and Machine Intelligence, 1989, pp. 567-585, vol. II, No. 6.
Bookstein, F. L., Thin-Plate splines and the atlas problem for biomedical images, Information Processing in Medical Imaging, Lecture Notes in Computer Science, 1991, pp. 326-342, vol. 511/1991. (Abstract).

(56) References Cited

OTHER PUBLICATIONS

Park & Sanberg, Universal approximation using radial-basis-function networks, Neural Computation, 1991, pp. 246-257, vol. 3., No. 2. (Abstract).

Bors & Pitas, Median Radial Basis Functions Neural Network, IEEE Computational Intelligence Society, 1996, vol. 7, issue 6.

Bennink, H.E.; "Warping a Neuro-Anatomy Atlas on 3D MRI Data with Radial Basis Functions"; In: Proc. Intern. Conf. on Biomedical Engineering (Biomed) 2006, Kuala Lumpur, Malaysia; Reference pp. 1-4; Publication Date: Dec. 11-14, 2006.

Carr, J.C.; "Reconstruction and Representation of 3D Objects with Radial Basis Functions"; Annual Conference of Computer Graphics SIGGRAPH; Reference pp. 67-76; Publication Date: Aug. 2001.

Chui, Haili; "A new point matching algorithm for non-rigid registration"; Computer Vision and Understanding, vol. 69, Issues 2-3; Feb.-Mar. 2003.

Donato, Gianluca; "Approximate thin plate spline mappings"; Computer Vision—ECCV Lecture Notes in Computer Science, vol. 2352; Reference pp. 21-31; Publication Date: Apr. 2002.

Author: Masson, Lucie Title: Tracking 3D objects using flexible models Citation: BMVC Publication Date: Sep. 2005.

Wittkampf, Fred H.; "LocaLisa: New Technique for Real-Time 3-Dimensional localization of regular intracardiac electrodes"; Circulation—Journal of the American Heart Association; Reference pp. 1312-1317; Publication Date: Mar. 1999.

International Search Report and Written Opinion in PCT Application No. PCT/US2013/045885 (dated Oct. 1, 2013).

Kabra, Rajesh et al., "Recent trends in imaging for atrial fibrillation ablation", Indian Pacing and Electrophysiology Journal, pp. 215-227, May 5, 2010.

Reinsch, Christian; "Smoothing by Spline Functions"; Citation: 13 Numer. Math. Bd. 10 Reference pp. 177-183 Publication Date: Oct. 1967.

Title: Definition: interpolate Citation: Collins English Dictionary—Complete and Unabridged 10th Edition, 2009, Harper Collins Publishers Publication Date: 2009.

Title: International Search Report & Written Opinion Citation: PCT/US2012/030925 Publication Date: Jun. 20, 2012.

Supplementary European Search Report in EP Application No. 12831765.8 (dated Mar. 10, 2015).

Supplementary Partial European Search Report in EP Application No. 12770539.0 (dated Dec. 4, 2014).

Roussos et al., "Rapid evaluation of radial basis functions," Journal of Computational and Applied Mathematics 180 (2005) 51-70.

"3D Photography: Point Based Rigid Registration," Retrieved from http://www1.cs.columbia.edu/~allen/PHOTOPAPERS/hmwk1.pdf, Aug. 15, 2017.

\* cited by examiner

SYSTEM AND METHOD FOR REGISTRATION OF MULTIPLE NAVIGATION SYSTEMS TO A COMMON COORDINATE FRAME

CROSS-REFERENCE TO RELATED APPLICATIONS

This application is related to U.S. application Ser. No. 11/715,923, filed 9 Mar. 2007 (now pending), which is hereby incorporated by reference as though fully set forth herein.

BACKGROUND OF THE INVENTION a. Field of the Invention

The instant invention relates to localization systems, such as those used in cardiac diagnostic and therapeutic procedures. In particular, the instant invention relates to a system and method for registering the coordinate frames of multiple such systems (e.g., a magnetic-based system and an impedance-based system) to common coordinate frames.

b. Background Art

The three-dimensional coordinates of a catheter or other medical device moving within a patient's body are often tracked using a localization system (sometimes also referred to as a "mapping system," "navigation system," or "positional feedback system"). These devices typically use magnetic, electrical, ultrasound, and other radiation sources to determine the coordinates of these devices. For example, impedance-based localization systems determine the coordinates of the medical device by interpreting a voltage measured by the medical device as a location within an electrical field.

Each different type of localization systems offers certain advantages and disadvantages. For example, an impedance-based localization system offers the ability to track numerous localization elements simultaneously, but is susceptible to inhomogeneities in the electrical field and "drift" resulting from varying impedance regions and other external factors. As used herein, the term "drift" refers to a stationary localization element appearing to move due, for example, to patient movement, respiration, electrical noise, varying impedance, and other external factors. Certain solutions to the disadvantages associated with inhomogeneous electrical fields and drift are described in U.S. application Ser. Nos. 11/227,580, filed 15 Sep. 2005; Ser. No. 11/715,919, filed 9 Mar. 2007; and Ser. No. 12/986,409, filed 7 Jan. 2011, all of which are incorporated by reference as though fully set forth herein.

Likewise, a magnetic-based system offers the advantages of improved homogeneity and less drift than an impedance-based system. Such systems, however, require special sensors to be used as localization elements and, as such, are relatively limited in the number of localization elements that can be simultaneously tracked.

BRIEF SUMMARY OF THE INVENTION

It would therefore be advantageous to develop a hybrid localization system that leverages the advantages, while minimizing the disadvantages, of several individual localization systems. For example, a hybrid magnetic- and impedance-based localization system could simultaneously track a large number of localization elements using the impedance-based system while minimizing the effect of inhomogeneities and drift by using the magnetic-based system.

Because each localization system measures the position of its respective localization elements within its respective localization field relative to a unique coordinate frame, however, localization elements that are coincident in real space (that is, they occupy substantially the same physical location) may not appear coincident if rendered on a display device by such a hybrid localization system. It would therefore also be advantageous to provide a transformation that accurately transforms position measurements for the various localization elements to a common coordinate frame.

Disclosed herein is a method of registering two or more localization systems utilizing unique coordinate frames to a common coordinate frame. The method includes the following steps: using a first localization system having a first coordinate frame A to measure position information for a first reference location, the measured position information being $A_1$; using a second localization system having a second coordinate frame B to measure position information for the first reference location, the measured position information being $B_1$; associating the position information for the first reference location measured by the first and second localization systems, respectively, as a first fiducial grouping $(A_1, B_1)$; using the first localization system to measure position information for a second reference location, the measured position information being $A_2$; using the second localization system to measure position information for the second reference location, the measured position information being $B_2$; associating the position information for the second reference location measured by the first and second localization systems, respectively, as a second fiducial grouping $(A_2, B_2)$; using at least the first and second fiducial groupings $(A_1, B_1)$ and $(A_2, B_2)$ to generate a mapping function $f$ that transforms position measurements made using the second localization system relative to the second coordinate frame B to the first coordinate frame A, wherein the mapping function $f$ is defined such that, for any reference location r for which position information is measured using the first and second localization systems as $A_r$ and $B_r$, respectively, a distance between $f(B_r)$ and $A_r$ is about zero. Preferably, the distance between $f(B_r)$ and $A_r$ is less than about 2 mm. The first and second localization systems can be magnetic-based and impedance-based localization systems, respectively.

In some aspects, the mapping function $f$ employs a non-linear registration algorithm. Suitable non-linear registration algorithms include thin plate splines algorithms and radial basis function networks algorithms.

Also disclosed herein is a method of measuring position information for a medical device within a patient's body, including the steps of: establishing a first localization field using a first localization system having a first coordinate frame A; establishing a second localization field using a second localization system having a second coordinate frame B; measuring position information for a plurality of reference locations r relative to the first and second coordinate frames using the first and second localization systems, respectively; associating the measured position information for each of the plurality of reference locations r as a plurality of fiducial groupings, wherein each fiducial grouping comprises position information for a single reference point r measured using the first and second localization systems, respectively, as $(A_r, B_r)$; and using the plurality of fiducial groupings to generate a mapping function $f$ such that, for each reference location r, $f(B_r)$ is about equal to $A_r$. The method optionally includes: measuring position information for the medical device as it moves through the patient's body relative to the second coordinate frame using the second localization system; and converting the measured position information for the medical device as it moves through the patient's body into the first coordinate frame using the mapping function $f$.

In some embodiments, the invention provides methods of monitoring, signaling, and adjusting or mitigating for various anomalies, such as dislodgement or drift of a fixed reference localization element. Thus, the method optionally includes the following steps: defining a fixed reference localization element for the first localization system, the fixed reference localization element for the first localization system having a position measured relative to coordinate frame A of $R_A$; defining a fixed reference localization element for the second localization system, the fixed reference localization element for the second localization system having a position measured relative to coordinate frame B of $R_B$; computing $f(R_B)$; computing a divergence between $f(R_B)$ and $R_A$; and signaling an anomaly if the divergence between $f(R_B)$ and $R_A$ exceeds a divergence threshold. The fixed reference localization elements for the first and second localization systems may be substantially coincident in real space (i.e., they are physically coincident or nearly coincident). Anomalies may be mitigated by computing offset vectors and/or generating new mapping functions $f'$.

Another approach to monitoring for anomalies includes the following steps: defining a primary reference localization element; defining a secondary reference localization element; defining a tertiary reference localization element; measuring position information for the primary localization element and the secondary localization element with respect to the coordinate frame A; measuring position information for the tertiary reference localization element with respect to both of the coordinate frame A and the coordinate frame B; using the mapping function $f$ to convert the position information of the tertiary reference localization element measured with respect to coordinate frame B to the coordinate frame A; computing divergences between the position information for the primary reference localization element measured with respect to the coordinate frame A and at least one of: the position information for the secondary reference localization element measured with respect to the coordinate frame A; the position information for the tertiary reference localization element measured with respect to the coordinate frame A; and the position information for the tertiary reference localization element converted to the coordinate frame A; and signaling an anomaly if one or more of the computed divergences exceeds a divergence threshold.

The present invention also provides a hybrid localization system including: a magnetic-based localization system that measures localization element positions with respect to a coordinate frame A; an impedance-based localization system that measures localization element positions with respect to a coordinate frame B; a medical device including a plurality of localization elements, the plurality of localization elements comprising at least one localization element detectable by the impedance-based localization system and at least one localization element detectable by the magnetic-based localization system; at least one processor configured to express localization element positions measured by the impedance-based localization system with respect to the coordinate frame B in the coordinate frame A via application of a non-linear mapping function $f$. Optionally, the hybrid localization system further includes: a fixed reference localization element for the magnetic-based localization system, the fixed reference localization element for the magnetic-based localization system having a position, measured with respect to the coordinate frame A, of $R_A$; a fixed reference localization element for the impedance-based localization system, the fixed reference localization element for the impedance-based localization system having a position, measured with respect to the coordinate frame B, of $R_B$; and at least one processor configured to monitor a divergence between $R_A$ and $f(R_B)$ and to signal an anomaly when the divergence exceeds a divergence threshold.

The foregoing and other aspects, features, details, utilities, and advantages of the present invention will be apparent from reading the following description and claims, and from reviewing the accompanying drawings.

DETAILED DESCRIPTION OF THE INVENTION

The present invention provides a hybrid localization system and a method for registering different coordinate frames to a single, common coordinate frame. For purposes of illustration, the invention will be described in detail in the context of a hybrid localization system that includes both a magnetic-based localization system and an impedance-based localization system.

Each of the localization systems used in the hybrid localization system described below (e.g., the magnetic-based localization system and the impedance-based localization system) will have a unique coordinate frame in which it expresses position information. For illustrative purposes, the coordinate system of the magnetic-based system will be referred to as coordinate frame A, while that of the impedance-based system will be referred to as coordinate frame B. Typically, these coordinate frames will express position information as Cartesian coordinates, though the use of other coordinate systems, such as polar, spherical, and cylindrical, is also contemplated, as is the use of multiple coordinate systems (e.g., Cartesian and polar).

Though the present invention will be described in connection with cardiac procedures, and more particular in connection with a procedure carried out in a heart chamber, it is contemplated that the present invention may be practiced to good advantage in other contexts, such as tracking devices for placement of neurostimulation leads in a patient's brain. Further, though the present invention will generally be described in three dimensions and with respect to two localization systems, one of ordinary skill in the art will understand how to apply the principles disclosed herein in any number of dimensions and to any number of localization systems. Accordingly, the illustrative embodiment used herein to describe the invention should not be regarded as limiting.

Figure 1:
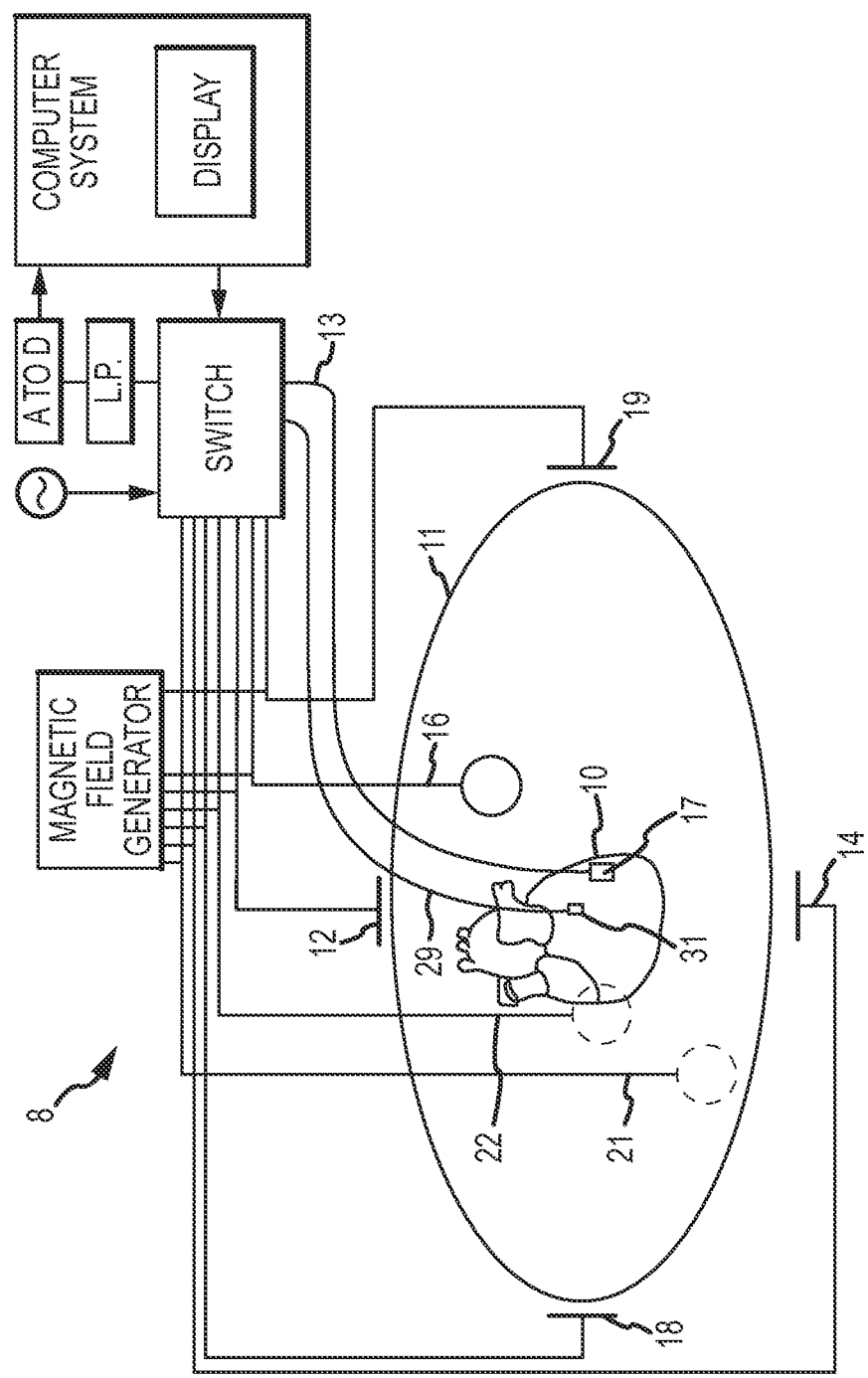
FIG. 1 is a schematic diagram of a hybrid localization system, such as may be used in an electrophysiology study.

FIG. 1 shows a schematic diagram of a hybrid localization system 8 for conducting cardiac electrophysiology studies by navigating a cardiac catheter and measuring electrical activity occurring in a heart 10 of a patient 11 (depicted, for simplicity's sake, as an oval) and three-dimensionally mapping the electrical activity and/or information related to or representative of the electrical activity so measured. As one of ordinary skill in the art will recognize, hybrid localization system 8 determines the location (and, in some aspects, the orientation) of objects, typically within a three-dimensional space, and expresses those locations as position information determined relative to at least one reference. System 8 can also be used to measure electrophysiology data at a plurality of points along a cardiac surface, and to store the measured data in association with location information for each measurement point at which the electrophysiology data was measured, for example to create a diagnostic data map of the patient's heart 10.

Hybrid localization system 8 includes two localization systems: an impedance-based localization system and a magnetic-based localization system. The ordinary artisan will readily appreciate the basic operation of such localization systems. Thus, they will only be explained herein to the extent necessary to understand the present invention.

In general, and as shown in FIG. 1, a localization system, such as an impedance- or magnetic-based localization system includes a plurality of localization field generators (e.g., 12, 14, 16, 18, 19, and 22) that generate an electrical or magnetic field, respectively, across the patient's body. These localization field generators, which may be applied to the patient (internally and/or externally) or fixed to an external apparatus, define three generally orthogonal axes, referred to herein as an x-axis, a y-axis, and a z-axis.

FIG. 1 depicts localization field generators 12, 14, 16, 18, 19, and 22 as coupled to both a current source and a magnetic source. It should be understood that this presentation is for simplicity of illustration. One of ordinary skill in the art will appreciate, of course, that each localization field generator will only be coupled to a source appropriate to the component localization system of which it is a part (e.g., impedance-based localization field generators will be coupled to the current source, while magnetic-based localization field generators will be coupled to the magnetic source).

Figure 2:
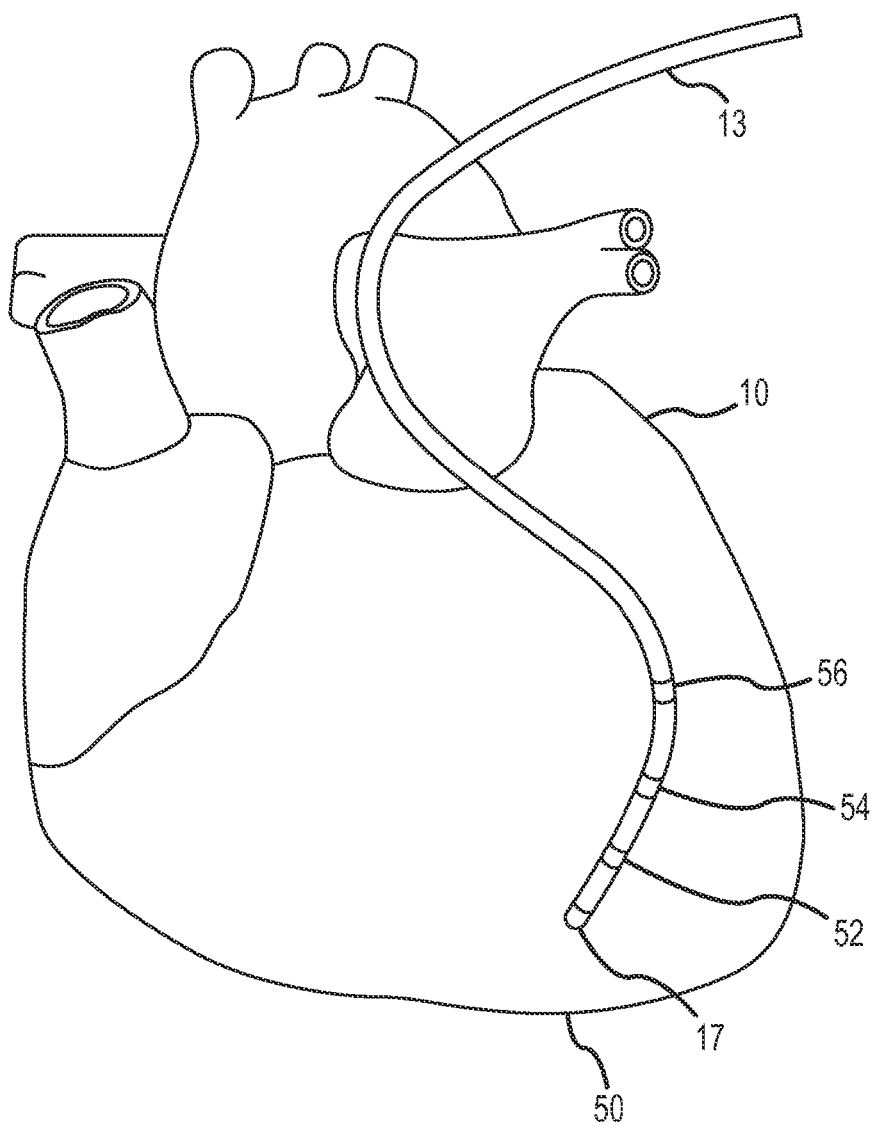
FIG. 2 depicts an exemplary catheter used in an electrophysiology study.

For purposes of this disclosure, an exemplary medical device, such as a catheter 13, is shown in FIG. 2. In FIG. 2, catheter 13 is depicted extending into the left ventricle 50 of the patient's heart 10. Catheter 13 includes a plurality of localization elements (e.g., 17, 52, 54, and 56) spaced along its length. As used herein, the term "localization element" generically refers to any element whose position within a localization field can be measured by that system (e.g., electrodes for an impedance-based system and magnetic sensors for a magnetic-based system).

Because each localization element lies within the localization field, location data may be collected simultaneously for each localization element. One of ordinary skill in the art will appreciate, of course, that an impedance-based localization system can simultaneously collect from a far larger number of localization elements than can a magnetic-based localization system.

For impedance-based localization systems, a reference electrode 21 (e.g., a "belly patch") can be used as a reference and/or ground electrode. Alternatively, a fixed intracardiac electrode 31 may be used as a reference electrode. This optional fixed reference electrode 31, which is shown in FIG. 1 as carried on a second catheter 29, can be attached to a wall of the heart 10 or anchored within the coronary sinus such that it is either stationary or disposed in a fixed spatial relationship with the localization elements. Thus, reference electrode 31 can be described as a "navigational reference," "local reference," or "fixed reference." Indeed, in many instances, fixed reference electrode 31 defines the origin of the impedance-based localization system's coordinate frame (e.g., coordinate frame B).

A magnetic-based localization system typically includes an element analogous to fixed reference electrode 31 to define the origin of the magnetic-based localization system's coordinate frame (e.g., coordinate frame A). That is, a magnetic-based localization system typically includes its own fixed reference relative to which the positions of localization elements 17, 52, 54, and 56 are measured. Such a reference can likewise be in a fixed internal or external location. Likewise, multiple references may be used for the same or different purposes (e.g., to correct for respiration, patient shift, system drift, or the like). Of course, impedance-based and/or magnetic-based localization systems may also include additional fixed references.

In a preferred embodiment, the impedance-based component of hybrid localization system 8 is the EnSite NavX™ navigation and visualization system of St. Jude Medical, Atrial Fibrillation Division, Inc. Suitable magnetic-based localization systems include the MediGuide Medical Positioning System (mGPS™) of St. Jude Medical, Atrial Fibrillation Division, Inc., the CARTO navigation and location system of Biosense Webster, Inc. and the AURORA® system of Northern Digital Inc.

A computer, which can comprise a conventional general-purpose computer, a special-purpose computer, a distributed computer, or any other type of computer, and which can comprise one or more processors, such as a single central processing unit (CPU), or a plurality of processing units, commonly referred to as a parallel processing environment, can control hybrid localization system 8 and/or execute instructions to practice the various aspects of the present invention described herein.

As one of ordinary skill in the art will appreciate, the position information measured by each component of hybrid localization system 8 is context-specific to that localization system. In other words, measurements made using the magnetic-based localization component of hybrid localization system 8 are expressed with respect to coordinate frame A, while those made using the impedance-based localization component of hybrid localization system 8 are expressed with respect to coordinate system B.

Figure 3:
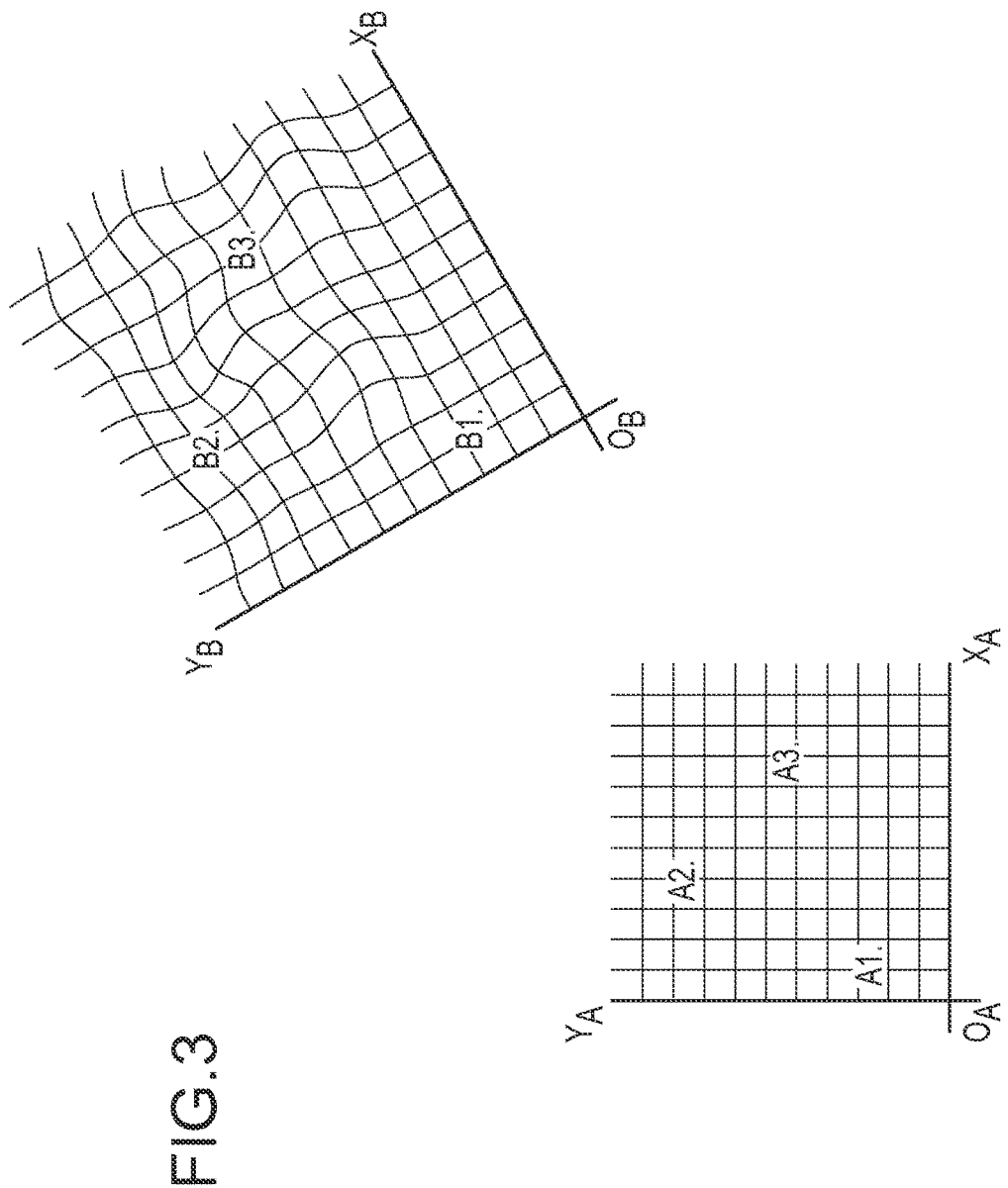
FIG. 3 illustrates position information of three reference points (e.g., fiducial points) measured relative to two different coordinate frames, as well as the inhomogeneity present in one of the coordinate frames.

This is illustrated (in two dimensions) in FIG. 3. FIG. 3 depicts coordinate axes $X_A$ and $Y_A$ for coordinate frame A (associated with the magnetic-based localization system) and coordinate axes $X_B$ and $Y_B$ for coordinate frame B (associated with the impedance-based localization system). The origins of coordinate frames A and B, $O_A$ and $O_B$, respectively, are offset from each other. In addition, the scales of coordinate frames A and B differ. Coordinate frames A and B are also rotated with respect to each other.

Three reference locations (as described further below) are identified with respect to each coordinate frame as A1, A2, and A3 in coordinate frame A and B1, B2, and B3 in coordinate frame B. As described in further detail below, the present invention warps coordinate frame B such that the locations of these reference locations coincide (that is, such that the coordinates of B1, B2, and B3 numerically match, or nearly match, the coordinates of A1, A2, and A3).

It is desirable, of course, to express all position measurements made by hybrid localization system 8 relative to a single, common coordinate frame. This is referred to as "registering" the components of hybrid localization system 8 to the common coordinate frame. For purposes of explanation, the coordinate frame of the magnetic-based localization system (e.g., coordinate frame A) will be considered the common coordinate frame (i.e., the frame to which all other localization systems in hybrid localization system 8 will be registered). It should be understood, however, that any coordinate frame may be used as the common coordinate frame.

The registration process utilizes reference locations for which position information is measured using both components of hybrid localization system 8. For example, the practitioner can navigate catheter 13 to a series of locations within heart 10, and, at each such reference location (denoted herein as r), the magnetic-based localization system can be used to measure position information relative to coordinate frame A (expressed as $A_r$) and the impedance-based localization system can be used to measure position information relative to coordinate frame B (expressed as $B_r$).

The reference locations r can be preselected (e.g., designated anatomical landmarks, such as the coronary sinus or pulmonary vein ostium) or arbitrary (e.g., any point on the surface of the heart, any point on a patient's body, any point on a patient table, or any point having a fixed or known relationship to a localization field generator). Similarly, they can be manually identified by the user (e.g., the user "clicks" when desired in order to capture position information for a reference location) or gathered automatically (e.g., hybrid localization system 8 periodically or episodically captures position information for a reference location, such as whenever the registered locations of the components of hybrid localization system 8 diverge by more than a preset tolerance).

For each reference location r, the position information measured with respect to each component of hybrid localization system 8 is associated as a fiducial grouping ($A_r$, $B_r$). Preferably, at least two such fiducial groupings (e.g., ($A_1$, $B_1$) and ($A_2$, $B_2$)) are used to generate a mapping function, denoted $f$, to the common coordinate frame. It is contemplated, however, that a single fiducial grouping may be used to perform an initial registration, particularly where coordinate frames A and B are not rotated relative to each other (e.g., as shown in FIG. 3). The mapping function $f$ is defined so as to transform the coordinates of a location, measured with the impedance-based localization system, into the common coordinate frame.

Of course, the various localization elements (e.g., the electrodes used in an impedance-based localization system and the magnetic sensors used in a magnetic-based localization system) may not be co-located on catheter 13, either by design or by necessity. It may be desirable to take this divergence into account when creating the fiducial groupings (A, $B_r$).

One method of accounting for this divergence is to interpolate position information measured by neighboring localization elements. For example, consider the case where catheter 13 is constructed such that magnetic sensors lie between neighboring electrodes and vice versa (that is, the localization elements alternate along the length of catheter 13). In the context of FIG. 2, suppose that localization elements 17 and 54 are electrodes and localization elements 52 and 56 are magnetic sensors.

To adjust for the divergence between localization elements, a series of "virtual electrodes" may be placed between neighboring electrodes (e.g., 17 and 54) to coincide with the position of the intervening magnetic sensors (e.g., 52). The location of this virtual electrode may be interpolated based upon the known geometry of catheter 13 and the measured positions of electrodes 17 and 54. The use of B-splines is contemplated. Fiducial groupings may then be created by associating virtual electrode position information with magnetic sensor position information.

Preferably, the mapping function $f$ is defined such that the mapping of a reference point r from coordinate frame B to coordinate frame A is coincident or near-coincident with the actual measured location of reference point r in coordinate frame A (e.g., $A_r$). Expressed mathematically, the mapping function $f$ is defined such that $|f(B_r)-A_r|\approx 0$ for all reference points r. A clinically-acceptable error (e.g., variation from 0 in the mapping function) is about 2 mm.

For linear and homogeneous localization systems, affine transformations (e.g., translation, rotation, and scaling), such as would result from application of a least mean square error fit (e.g., the Procrustes formulation), would be suitable. Such affine transformations require three or fewer fiducial groupings.

Because many localization systems—including impedance-based localization systems—are non-linear and non-homogenous, however, affine transformations are not as desirable in connection with the present invention. Preferably, therefore, the mapping function $f$ employs a non-linear registration algorithm to locally warp the coordinate frame of the impedance-based localization system at each reference location r to achieve an exact or near-exact match to the magnetic-based localization system. Such non-linear registration algorithms require four or more fiducial groupings.

There are a number of suitable non-linear registration algorithms for generating the mapping function $f$. One preferred algorithm is the thin plate splines algorithm, which is known for use in fusing images from one modality (e.g., MRI or CT) to a localization system (e.g., the EnSite NavX™ system), such as disclosed in U.S. application Ser. No. 11/715,923. Generally, the thin plate splines algorithm includes summing a fixed number of weighted basis functions. Typically, the number of weighted basis functions will be equal to the number of fiducial groupings. The following articles, which are hereby incorporated by reference as though fully set forth herein, describe the thin plate splines algorithm in further detail:

Bookstein, F L. Principal Warps: Thin Plate Splines and the Decomposition of Deformations. *IEEE Transactions on Pattern Analysis and Machine Intelligence.* 1989. 11:567-585.

Bookstein, F L. Thin-Plate Splines and the Atlas Problem for Biomedical Images. *Proceedings of the 12$^{th}$ International Conference on Information Processing in Medical Imaging.* July, 1991.

Another suitable non-linear registration algorithm is a mean value coordinates algorithm. A mean value coordinates algorithm generally transforms individual points in three dimensions to a closed, triangulated surface in three dimensions known as a "control mesh." When the control mesh is deformed, the algorithm can compute a smooth interpolation function through three dimensional space that exactly deforms the vertices and triangles without wildly extrapolating in regions far from the control mesh. The following article, which is hereby incorporated by reference as though fully set forth herein, describes mean value coordinates algorithms in further detail: Ju T, Schaefer S, Warren J, Mean Value Coordinates for Closed Triangular Meshes. *ACM Transactions on Graphics.* July 2005. 24(3): 561-66.

Still another suitable non-linear registration algorithm is the radial basis function networks algorithm, which is well known in neural networks. The following references describe radial basis function networks algorithms in further detail, and are hereby incorporated by reference as though fully set forth herein:

J. Moody and C. J. Darken, Fast Learning in Networks of Locally Tuned Processing Units. *Neural Computation.* 1989. 1, 281-294.

J. Park and I. W. Sandberg, Universal Approximation Using Radial-Basis-Function Networks. *Neural Computation.* 1991. 3(2):246-257.

A. G. Bors and I. Pitas, Median Radial Basis Function Neural Network, *IEEE Trans. On Neural Networks.* November 1996. 7(6):1351-1364.

Martin D. Buhmann and M. J. Ablowitz, Radial Basis Functions: Theory and Implementations. 2003.

Paul V. Yee and Simon Haykin, Regularized Radial Basis Function Networks: Theory and Applications. 2001.

Once the mapping function $f$ is generated, hybrid localization system 8 can track the position of catheter 13 within the patient's body using the higher bandwidth of the impedance-based localization system (e.g., measuring relative to coordinate frame B) while expressing the position using the more homogenous coordinate frame A of the magnetic-based localization system via application of the mapping function $f$. This allows hybrid localization system 8 to exploit the advantages of, while minimizing the disadvantages of, the constituent parts thereof.

Hybrid localization system 8 can also monitor for and signal various anomalies, such as dislodgement or drift in one or more of the magnetic- and/or impedance-based localization systems. That is, hybrid localization system 8 can keep track of whether the mapping function $f$ remains valid, and, if appropriate, correct for any anomalies or compute a new mapping function $f$.

For example, in one aspect of the disclosure, at least one fixed reference localization element is defined for each of the magnetic-based localization system and the impedance-based localization system. For purposes of illustration, the positions of these reference localization elements will be denoted as $R_A$ and $R_B$, respectively. Hybrid localization system 8 can continuously, periodically, or episodically compute $f(R_B)$ and compare that computation to $R_A$.

Assuming no anomalies (e.g., no drift and/or no dislodgement of one or more of the fixed reference localization elements), the divergence between $f(R_B)$ and $R_A$ should remain relatively constant. Typically, the fixed reference localization elements will be coincident in real space, such that the substantially constant divergence, assuming no anomalies, is approximately zero. It is contemplated, however, to have separate fixed reference localization elements with a non-zero, but known, divergence therebetween.

If, on the other hand, the divergence exceeds a divergence threshold, it can be considered an indication of an anomaly (e.g., drift in the impedance-based localization system and/or dislodgement of one or more of the fixed reference localization elements). The practitioner can be alerted to this anomaly, for example via audible and/or visible alarms emitted by hybrid localization system 8. Additionally, steps may be taken to mitigate the anomaly. For example, where the anomaly is a dislodgement of one or more fixed reference localization elements, an offset vector may be calculated to account for the dislodgement. (Offset vectors to correct for dislodgement of navigational references are described in U.S. application Ser. No. 12/972,253, filed 17 Dec. 2010, and Ser. No. 11/647,277, filed 29 Dec. 2006, both of which are hereby incorporated by reference as though fully set forth herein.) Alternatively, the mitigation may take the form of computing a new mapping function $f$, in effect re-doing the calibration described above, using either new fiducial groupings or previously saved fiducial groupings.

In another aspect, hybrid localization system 8 detects anomalies using three reference localization elements, designated as primary, secondary, and tertiary localization elements. Preferably, the primary reference localization element is rigidly associated with the localization field generators for the magnetic-based localization system, such as by securing it to a structure that carries the localization field generators. Preferably, the secondary reference localization element is disposed on the patient, while the tertiary reference localization element is disposed within the patient.

Position information for the primary and secondary reference localization elements are measured by the magnetic-based localization system relative to coordinate frame A. Position information for the tertiary reference localization element is measured using both the magnetic-based localization system (e.g., relative to coordinate frame A) and the impedance-based localization system (e.g., relative to coordinate frame B), the latter of which is converted to coordinate frame A via application of the mapping function $f$.

Three quantities in coordinate frame A can then be analyzed, relative to respective divergence thresholds, by hybrid localization system 8 to determine whether an anomaly has occurred:

(A) A divergence between the measured position information for the secondary reference localization element and the measured position information for the primary reference localization element;

(B) A divergence between the measured position information for the tertiary reference localization element and the measured position information for the primary reference localization element; and (C) A divergence between the converted position information for the tertiary reference localization element and the measured position information for the primary reference localization element.

These three quantities lead to eight cases, as shown in Table 1 ("N" indicates that the quantity does not exceed the respective divergence threshold, while "Y" indicates that it does):

TABLE 1

| Case | Quantity A | Quantity B | Quantity C |
|------|------------|------------|------------|
| 1 | N | N | N |
| 2 | N | N | Y |
| 3 | N | Y | N |
| 4 | N | Y | Y |
| 5 | Y | N | N |
| 6 | Y | N | Y |
| 7 | Y | Y | N |
| 8 | Y | Y | Y |

The cases are explained below:

Case 1: No anomalies detected; operate as normal.

Case 2: The impedance-based system has changed relative to the magnetic-based system, but there has been no change in the magnetic-based system. The anomaly is limited to the impedance-based system, and is likely drift (if it was dislodgement, Quantity B would also show a "Y"—see Case 4). The preferred mitigation is to compute an offset vector to account for this drift.

Case 3: This is an unusual case, as the circumstances under which there would be a divergence in Quantity B but not Quantity C are very narrow (e.g., a dislodgement of the tertiary reference localization element and simultaneous, offsetting drift in the impedance-based localization system). The more likely explanation is that both systems have experienced an unknown anomaly, making navigation unreliable. Accordingly, the preferred mitigation is to compute a new mapping function $f$ using newly-collected fiducial groupings.

Case 4: In case 4, the anomaly is likely a physical dislodgement of the tertiary reference localization element. The preferred mitigation is to compute an offset vector to account for the dislodgement.

Case 5: The position of the secondary reference localization element has changed, likely due to movement of the patient on the table. The preferred mitigation is to compute an offset vector to account for patient movement.

Cases 6-8: These cases indicate simultaneous shift of two reference localization elements. Events such as electrical cardioversion could give rise to these cases. The preferred mitigation is to compute a new mapping function $f$ using newly-collected fiducial groupings.

Although several embodiments of this invention have been described above with a certain degree of particularity, those skilled in the art could make numerous alterations to the disclosed embodiments without departing from the spirit or scope of this invention. For example, although the invention has been described in the context of a hybrid magnetic- and impedance-based localization system, the principles disclosed herein could be extended to other localization systems, including, without limitation, MRI-based localization systems, fluoroscopy-based localization systems, and intra-cardiac echocardiography-based localization systems.

Similarly, although the present invention has been described in connection with registration of only two localization systems to a common coordinate system, the teachings herein are equally applicable to the registration of any number of localization systems to a common coordinate system, with each localization system having its own mapping function that transforms position measurements from the coordinate system of that localization system to the common coordinate system.

All directional references (e.g., upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other.

It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. A method of registering two or more localization systems utilizing unique coordinate frames to a common coordinate frame, comprising:
   using a first localization system having a first coordinate frame A to measure position information for a first reference location, the measured position information being $A_1$;
   using a second localization system having a second coordinate frame B to measure position information for the first reference location, the measured position information being $B_1$;
   associating the position information for the first reference location measured by the first and second localization systems, respectively, as a first fiducial grouping ($A_1$, $B_1$);
   using the first localization system to measure position information for a second reference location, the measured position information being $A_2$;
   using the second localization system to measure position information for the second reference location, the measured position information being $B_2$;
   associating the position information for the second reference location measured by the first and second localization systems, respectively, as a second fiducial grouping ($A_2$, $B_2$);
   using at least the first and second fiducial groupings ($A_1$, $B_1$) and ($A_2$, $B_2$) to generate a mapping function $f$ that transforms position measurements made using the second localization system relative to the second coordinate frame B to the first coordinate frame A;
   defining a primary reference localization element;
   defining a secondary reference localization element;
   defining a tertiary reference localization element;
   measuring position information for the primary localization element and the secondary localization element with respect to the first coordinate frame A;
   measuring position information for the tertiary reference localization element with respect to both of the first coordinate frame A and the second coordinate frame B;
   using the mapping function $f$ to convert the position information of the tertiary reference localization element measured with respect to the second coordinate frame B to the first coordinate frame A;
   computing divergences between the position information for the primary reference localization element measured with respect to the first coordinate frame A and at least one of:
      the position information for the secondary reference localization element measured with respect to the first coordinate frame A;
      the position information for the tertiary reference localization element measured with respect to the first coordinate frame A; and
      the position information for the tertiary reference localization element converted to the first coordinate frame A; and
   signaling an anomaly if one or more of the computed divergences exceeds a divergence threshold.

2. The method according to claim 1, wherein the first localization system is a magnetic-based localization system and the second localization system is an impedance-based localization system.

3. The method according to claim 1, wherein each of the primary reference localization element, the secondary reference localization element, and the tertiary reference localization element comprises a fixed reference localization element.

4. The method according to claim 1, wherein the mapping function $f$ is defined such that, for any reference location r for which position information is measured using the first and second localization systems as $A_r$ and $B_r$, respectively, a distance between $f(B_r)$ and $A_r$ is about zero.

5. The method according to claim 4, wherein the distance between $f(B_r)$ and $A_r$ is less than about 2 mm.

6. The method according to claim 1, wherein the mapping function $f$ employs a non-linear registration algorithm.

7. The method according to claim 6, wherein the non-linear registration algorithm comprises a thin plate splines algorithm.

8. The method according to claim 6, wherein the non-linear registration algorithm comprises a radial basis function networks algorithm.

9. A method of measuring position information for a medical device within a patient's body, comprising:
    establishing a first localization field using a first localization system having a first coordinate frame A;
    establishing a second localization field using a second localization system having a second coordinate frame B;
    measuring position information for a plurality of reference locations r relative to the first and second coordinate frames using the first and second localization systems, respectively;
    associating the measured position information for each of the plurality of reference locations r as a plurality of fiducial groupings, wherein each fiducial grouping comprises position information for a single reference point r measured using the first and second localization systems, respectively, as $(A_r, B_r)$;
    using the plurality of fiducial groupings to generate a mapping function $f$ such that, for each reference location r, $f(B_r)$ is about equal to $A_r$;
    defining a fixed reference localization element for the first localization system, the fixed reference localization element for the first localization system having a position measured relative to coordinate frame A of $R_A$;
    defining a fixed reference localization element for the second localization system, the fixed reference localization element for the second localization system having a position measured relative to coordinate frame B of $R_B$;
    computing $f(R_B)$;
    computing a divergence between $f(R_B)$ and $R_A$; and
    signaling an anomaly if the divergence between $f(R_B)$ and $R_A$ exceeds a divergence threshold.

10. The method according to claim 9, further comprising:
    measuring position information for the medical device as it moves through the patient's body relative to the second coordinate frame using the second localization system; and
    converting the measured position information for the medical device as it moves through the patient's body into the first coordinate frame using the mapping function $f$.

11. The method according to claim 9, wherein the fixed reference localization element for the first localization system and the fixed reference localization element for the second localization system are coincident in real space.

12. The method according to claim 9, wherein the step of signaling an anomaly comprises signaling that at least one of the fixed reference localization elements has become dislodged.

13. The method according to claim 9, wherein the step of signaling an anomaly comprises signaling that at least one of the localization systems is experiencing drift.

14. The method according to claim 9, further comprising:
    defining a primary reference localization element;
    defining a secondary reference localization element;
    defining a tertiary reference localization element;
    measuring position information for the primary localization element and the secondary localization element with respect to the coordinate frame A;
    measuring position information for the tertiary reference localization element with respect to both of the coordinate frame A and the coordinate frame B;
    using the mapping function $f$ to convert the position information of the tertiary reference localization element measured with respect to coordinate frame B to the coordinate frame A;
    computing divergences between the position information for the primary reference localization element measured with respect to the coordinate frame A and at least one of:
        the position information for the secondary reference localization element measured with respect to the coordinate frame A;
        the position information for the tertiary reference localization element measured with respect to the coordinate frame A; and
        the position information for the tertiary reference localization element converted to the coordinate frame A; and
    signaling an anomaly if one or more of the computed divergences exceeds a divergence threshold.

15. The method according to claim 9, wherein the first localization system comprises a magnetic-based localization system and the second localization system comprises an impedance-based localization system.

16. The method according to claim 9, wherein the mapping function comprises a non-linear registration of the coordinate frame B to the coordinate frame A.

17. The method according to claim 9, further comprising mitigating the anomaly.

18. The method according to claim 17, wherein the mitigating step comprises computing an offset vector to account for the anomaly.

19. The method according to claim 17, wherein the mitigating step comprises generating a new mapping function $f'$.

20. A hybrid localization system, comprising:
    a magnetic-based localization system that measures localization element positions with respect to a coordinate frame A;
    an impedance-based localization system that measures localization element positions with respect to a coordinate frame B;
    a medical device including a plurality of localization elements, the plurality of localization elements comprising at least one localization element detectable by the impedance-based localization system and at least one localization element detectable by the magnetic-based localization system;
    at least one processor configured to express localization element positions measured by the impedance-based localization system with respect to the coordinate frame B in the coordinate frame A via application of a non-linear mapping function $f$;
    a fixed reference localization element for the magnetic-based localization system, the fixed reference localization element for the magnetic-based localization system having a position, measured with respect to the coordinate frame A, of $R_A$;
    a fixed reference localization element for the impedance-based localization system, the fixed reference localization element for the impedance-based localization system having a position, measured with respect to the coordinate frame B, of $R_B$; and at least one processor configured to monitor a divergence between $R_A$ and $f(R_B)$ and to signal an anomaly when the divergence exceeds a divergence threshold.

\* \* \* \* \*